United States Patent
Samson

Patent Number: 5,370,691
Date of Patent: Dec. 6, 1994

[54] INTRAVASCULAR INFLATABLE STENT

[75] Inventor: Gene Samson, Milpitas, Calif.

[73] Assignee: Target Therapeutics, Inc., Fremont, Calif.

[21] Appl. No.: 11,480

[22] Filed: Jan. 26, 1993

[51] Int. Cl.⁵ .............................................. A61F 2/04
[52] U.S. Cl. ....................................... 623/12; 606/194
[58] Field of Search ................... 606/192–194; 623/1, 12; 600/31

[56] References Cited

U.S. PATENT DOCUMENTS

| | | | |
|---|---|---|---|
| 4,341,218 | 7/1982 | Ü128 | 325/ |
| 4,638,803 | 1/1987 | Rand | 128/325 |
| 4,776,337 | 10/1988 | Palmax | 128/343 |
| 4,800,882 | 1/1989 | Gianturco | 128/343 |
| 4,881,939 | 11/1989 | Newman | 600/31 |
| 4,886,062 | 12/1989 | Wiktor | 128/343 |
| 4,923,464 | 5/1990 | DiPisa, Jr. | 606/195 |
| 4,950,227 | 8/1990 | Savin et al. | 604/8 |
| 5,041,090 | 8/1991 | Scheglov et al. | 604/101 |
| 5,135,535 | 8/1992 | Kramer | 606/192 |
| 5,139,480 | 8/1992 | Hickle et al. | 604/8 |
| 5,156,620 | 10/1992 | Pigott | 623/1 |
| 5,163,951 | 11/1992 | Pinchuk et al. | 623/1 |
| 5,171,261 | 12/1992 | Noishiki et al. | 623/1 |
| 5,226,888 | 7/1993 | Arney | 604/96 |

FOREIGN PATENT DOCUMENTS

WO92/09246 6/1992 WIPO.
9218195 10/1992 WIPO.

*Primary Examiner*—Jerome L. Kruter
*Attorney, Agent, or Firm*—Morrison & Foerster

[57] ABSTRACT

This invention is an intraluminal stent or graft suited for the noninvasive treatment of aneurysms, diseased blood vessels, and other bodily lumen. The stent is made up of polymeric tubing which is helically and tightly wound to produce a column having an open lumen from one end to the other. At the stent's distal end, the tubing is sealed. At the stent's proximal end, the stent is adapted to allow the introduction of fluid suitable for inflating the stent at the chosen vascular site. The stent coils adhere to each other or to one or more sizing strips which may be straight or helical in configuration, or the stent may be constructed to use both methodologies.

11 Claims, 2 Drawing Sheets

INTRAVASCULAR INFLATABLE STENT

FIELD OF THE INVENTION

This invention is a intraluminal stent or graft suited for the noninvasive treatment of aneurysms, diseased blood vessels, and other bodily lumen. The stent is made up of polymeric tubing which is helically and tightly wound to produce a column having an open lumen from one end to the other. At the stent's distal end, the tubing is sealed. At the stent's proximal end, the stent is adapted to allow the introduction of fluid suitable for inflating the stent at the chosen vascular site. The stent coils adhere to each other or to one or more sizing strips which may be straight or helical in configuration, or the stent may be constructed to use both methodologies.

BACKGROUND OF THE INVENTION

This invention is an inflatable stent which may be used within various portions of the body's vasculature.

In general, stents are prosthetic devices which may be introduced into a body cavity such as the lumen of a blood vessel or in some other difficultly accessible place. Stents are tubular bodies having a diameter which may be increased or decreased once they are properly positioned in the region where they are to be left. Stents are particularly useful for permanently widening a vessel which is either in a narrowed condition or has been damaged by aneurysm. Stents are typically introduced into the vasculature or other body cavity by the use of a catheter.

There are a variety of different stent designs. By far most of them are made of metal wire or ribbon. For instance, WO 92/02,246, owned by Numed, Inc., shows a radially expandable stent made from fine wire formed into a serpentine ribbon wound into a cylindrical shape for introduction into a body vessel. The stent is placed within the vessel over a balloon which, when expanded, expands the stent in a radial fashion to support the wall of the vessel in the expanded configuration. This stent is said to be useful in the transluminar implantation of a stent for use in coronary angioplasty to prevent restenosis.

Other disclosures of expandable intraluminal stents involving radially expanding wire mesh include U.S. Pat. No. 4,776,337, to Palmaz. The patent shows a tubular member which may be made of a variety of different things supported by a gridlike collection of metal or plastic wires. U.S. Pat. No. 4,800,882, to Gianturco, shows a wire stent made of a number of curved sections that are formed into a generally circular configuration.

None of these disclosures suggest a helically coiled inflatable stent such as is disclosed here.

SUMMARY OF THE INVENTION

This invention is an intralumenal stent or graft suited for the noninvasive treatment of aneurysms and diseased blood vessels and other bodily lumen needing such a prosthesis. The stent is made of a thin-wall highly flexible polymeric tube wound in a helical configuration. One end of the tube so wound is sealed and is typically placed distally of the catheter device used to introduce the stent into the human vasculature. The proximal end of the stent tubing is equipped with a one-way valve to allow introduction of suitable inflating fluid into the stent and to inflate it to its final size within the vascular site. The stent is in a collapsed or crushed form when initially introduced to the chosen site and grows in diameter as it is inflated.

The stent is produced by winding the flexible polymeric tubing about an appropriate mandrel and self-welding the device either among adjacent coils or by the use of other thermoplastic strips placed along the outer or inner surfaces of the resulting stent. The choice of the manner in which the stent is assembled results in a variety of stents having a variety of different, ultimately flexible, shapes.

Figure 1A:
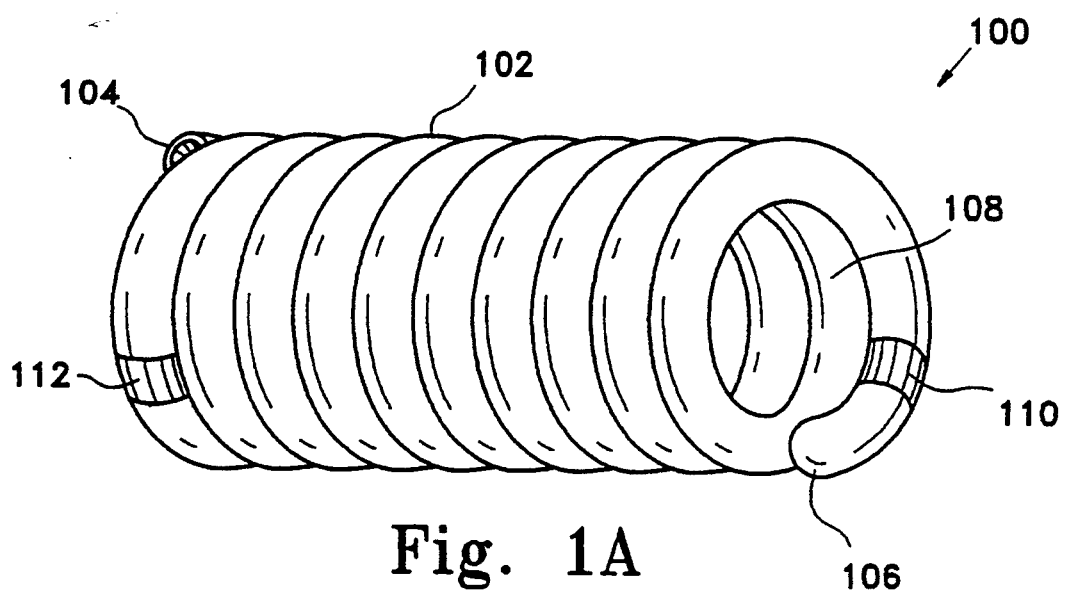
FIG. 1A is an enlarged sideview of a variation of the inventive stent.

My convention in these drawings is to place the end of the stent which is proximal to the introduction site in the body to the left of the drawing and the distal end of the device to the right side of the drawing.

DESCRIPTION OF THE INVENTION

As has been noted above, this invention is an intravascular inflatable stent which is produced by winding polymeric tubing into a generally helical shape and treating the thus-wound helix in some fashion so to produce a device which is inflatable and deflatable and does not unwind. This may be done by a variety of methods discussed below, including gluing, heating, and via the use of sizing strips. This device is typically used in the treatment of aneurysms and other vascular irregularities of a similar type.

The most common noninvasive therapy for aneurysms is through the process of filling the aneurysm sac with one of a variety of fillers such as detachable expandable micro-balloons and platinum coils. Each of these procedures, however, require the placement of the material into the aneurysm sac via the neck of the aneurysm. These methods therefore run the substantial risk of rupturing the wall of the sac and causing severe hemorrhaging. Obviously, this is especially true if the wall of the aneurysm is extremely thin. The amount of material necessary to fill the aneurysm completely is often difficult to determine. Use of too large an amount may result in migration of the introduced material into other segments of the vasculature thereby causing the production of emboli or vessel blockage.

Many aneurysms occur in tortuous segments of the vasculature. Access to aneurysm sites can be extremely difficult. The delivery of metallic stents by expandable angioplasty balloon catheters has been proposed as a treatment for aneurysms. However, because of the relative stiffness of the catheter configuration using both a stent and a balloon, access to the aneurysm site is difficult if not impossible. The irregular surface of most metallic stents is also likely to damage the endothelial wall of healthy arteries during delivery. Finally, it is unlikely that the blood vessel from which the aneurysm arises is straight in the region of the aneurysm. Therefore, the stent ideally should have some flexibility along its axis so to conform to the curvature of the vessel at the aneurysm site.

FIG. 1A is an enlargement of the basic configuration of the inventive stent device. The stent assembly, denoted as (100) in FIG. 1A, is a tightly, helically wound polymeric tubing (102) having a proximal end to the tubing (104) and a distal end to the tubing (106). The tubing is tightly wound into a column having an inner lumen (108), which lumen extends from one end of the column to the other. By tightly wound, I mean to say that the coils, as wound, are adjacent each other prior to inflation. The proximal tubing end (104) is equipped with a one-way valve (shown in detail in FIG. 1B), and the distal end (106) is sealed. Also shown in FIG. 1A are optional radiopaque markers (110) on the distal end and (112) on the proximal end. These may be bands of some radiopaque metal, which also possesses long-term biocompatibility and may be slipped onto the constituent tubing before treatment to stabilize the coil shape. The radiopaque markers (110) and (112) are optional, but practically are necessary to determine the position of the stent during its installation. Other methods of determining the position of the stent are, of course, known, and are useful here.

The polymer used in the tubing for this stent may be any of a variety of biocompatible polymers which are readily inflatable. For instance, thermoplastics such as high-density polyethylene, low-density polyethylene, and polypropylene, as well as interpolymers and block copolymers of these polyolefins are suitable. Elastomers, such as silicones or natural or synthetic rubbers are not usually desirable. Other polymers such as polyacrylonitrile, polyethylene terephthalate, and polybutylene terephthalate are also suitable materials. The radiopaque markers may be any suitable radiopaque material, preferably metal. Materials such as the platinum series of metals (platinum, palladium, etc.) and gold, silver, and tantalum may be used as these markers. Certain stainless steels are also suitable for use as markers.

This variation may be made in the following way using polyethylene tubing as the exemplary preliminary material. Extruded polyethylene tubing is first treated with about 25 megarads of electron radiation to increase the polyethylene's softening temperature from about 350° F. to about 550° F. One end, the distal end, may be sealed by hot melt fusion and a platinum marker ring wrapped about the tubing near the tubing distal end. The tubing is then wound over a mandrel. The mandrel may be a variety of materials, e.g., a section of TEFLON tubing or a metal form. The whole assembly may be heated to about 525° F. and heat soaked as the adjacent tubing surfaces merge. After cooling, the mandrel is removed. Another platinum marker ring is fused to the other end of the tubing using a small wire mandrel within the tubing to maintain the patency of the lumen during such installation. A one-way valve is then secured proximally of the platinum marker band. Excess tubing is trimmed.

Figure 1B:
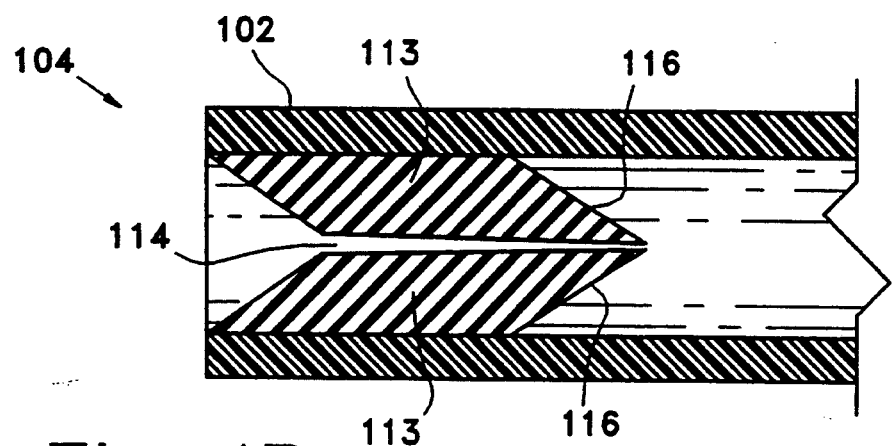
FIG. 1B is an enlarged sideview of a variation of the inlet one-way valve used in the inventive stent.

FIG. 1B is a close-up, partial sectional drawing of e one-way valve (104), as might be installed at the proximal end of stent (100). Tubing (102) is shown both in FIG. 1A and FIG. 1B. A small amount of a fusable thermoplastic is placed within the end of tubing (102) and a flat form is placed within this globule of meltable plastic. The material is then melted within the tip of tubing (102) and a slit is formed between the two half-sections (112) which adhere to the inner surface of the wall of tubing (102). The shape of half-sections (113) ideally is such that a surface (116) tends to close the slit upon application of pressure within the tubing (104). This tends to close valve assembly (103) as pressure is applied within tubing (102). The opening onto the front of the valve (114) preferably is shaped in such a way that it provides ready and easy access by a probe or other fitting introduced into the valve.

Figure 2:
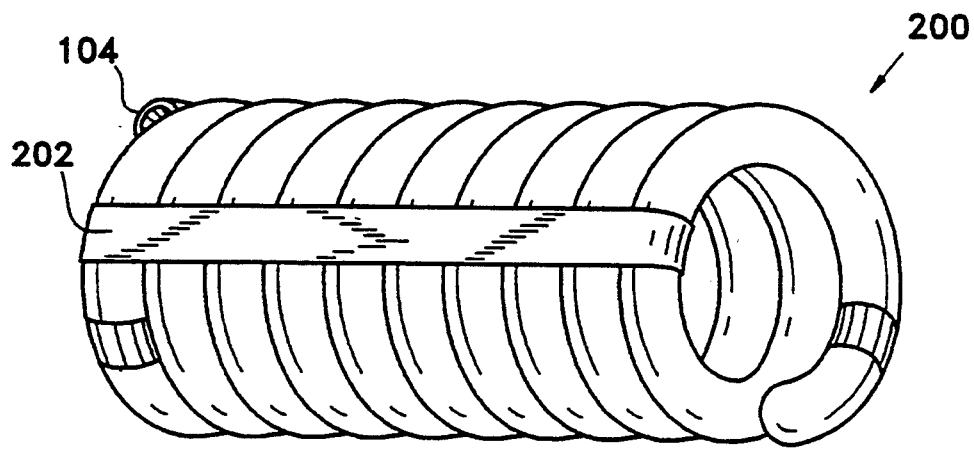
FIGS. 2, 3A, and 3B are enlarged side views of three variations of the inventive stent.

FIG. 2 shows a variation (200) of the device portrayed in FIG. 1. All of the components described above with relation to stent (100) in FIG. 1A are also found in this variation. The difference lies in the use of a sizing strip (202) along the axis of the stent and placed inside the lumen or outside on the outer lumen diameter. This sizing strip (202) provides a reasonably constant length of polymeric material which adheres to the coils along the sizing strip's length and keeps them from unwrapping.

The FIG. 2 stent variation (200) is made in a similar way to that described in relation to FIG. 1. However, after the extruded polyethylene tubing is irradiated to increase its softening temperature, a thin strip of nonirradiated polyethylene is laid on the mandrel (if an inside sizing strip is desired) or outside the wound stent (if an outer sizing strip is desired). More than one sizing strip may be used and, depending upon their intended use and the nature of the vascular site into which the stent is to be placed, may be placed in a variety of sites. The whole set-up is then heated only to about 400° F. until the plastic strip or strips is melted and fused with tubing. The finishing steps are then the same.

Use of a stent having a single sizing strip on one side may result in a stent having the ability to bend very far in one direction to close the neck of an aneurysm on the inside of a radius of a bending artery. The other side of the nonadhering side may open as the stent is inflated. Said another way, the stent would be closed on the inside of the turn and the stent would be open on the outer side of the bending radius.

Figure 3A:
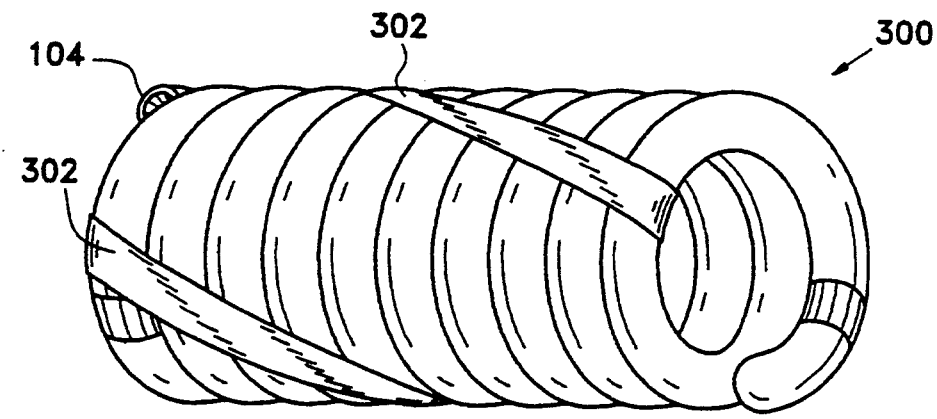

FIG. 3A shows still another variation of the invention in which tile sizing strips are placed helically about the wound tubing helix. As with the FIG. 2 device, the device (300) employs all of the components found in the FIG. 1A device (100). The sizing strips (302) are placed helically about the wound stent prior to moderate heat treatment. In this way, the stent, while partially flexible, is somewhat less so because of the presence of the helical sizing strips. The variations shown in FIG. 2 at 3 may utilize a single sizing strip inside or outside of the stent lumen or outside diameter, or multiple strips in or out. In especially troublesome situations where a relatively stiff stent is desirable, stents having criss-crossing sizing strips may be employed.

Figure 3B:
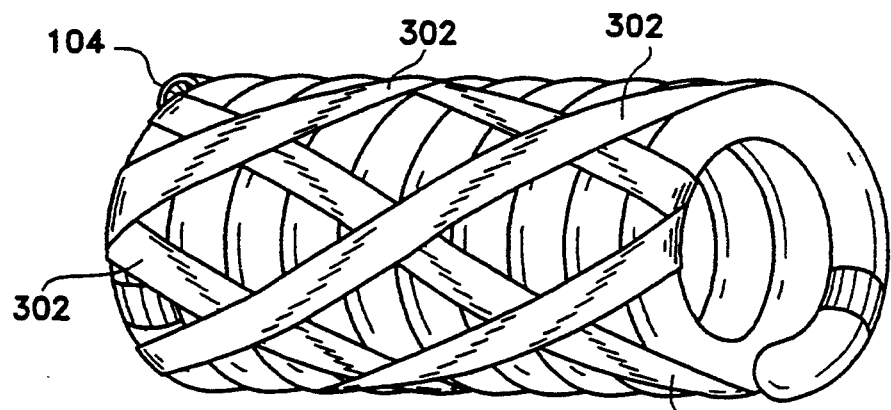

FIG. 3B shows a device similar to that shown in FIG. 3A in which the sizing strips (302) cross in order to provide the least amount of compliance for the resulting inventive stent.

The stent may be suitably reduced in size for introduction using a catheter in a variety of ways. The result of one such way is found in FIG. 4A. There, one of the variations shown in FIGS. 1A, 2, 3A, or 3B is placed on a mandrel such as a steel mandrel or other suitably strong round surface and collapsed or rolled so as to reduce the outer diameter of the stent and thus maintain the presence of an inner false lumen (402) after the completion of the crushing operation. This allows the stent to be used in a catheter with a guidewire or other device which must pass through the interior of the stent during its residency in the catheter.

Figures 4A, 4B:
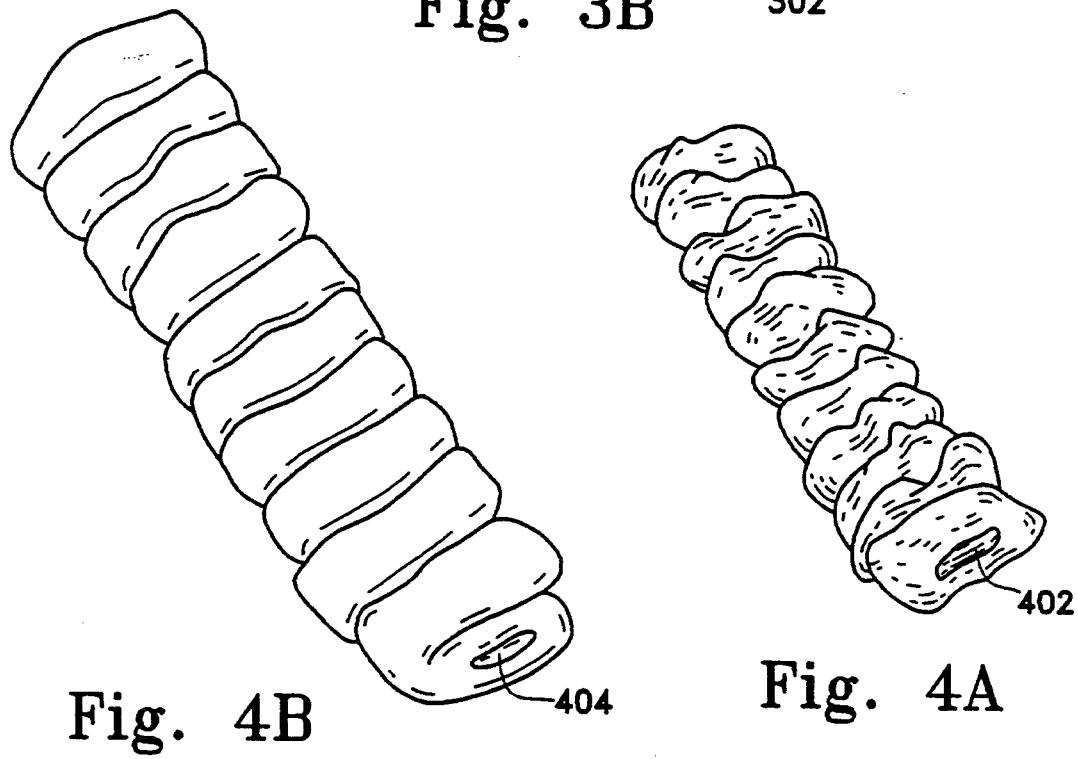
FIGS. 4A and 4B show generically the variations shown in the earlier figures respectively in a collapsed or crushed variation or in a folded configuration.

FIG. 4B shows a similar reduced configuration in which the stent of any of the configurations above is folded about a mandrel (404) (which mandrel is later removed) to form a false lumen. This mandrel may be TEFLON beading or other similar materials which are generally unaffected by moderate heat treatment and thus are removable. The wrapped, crushed, or folded stent with included mandrel is often placed within another forming means such as TEFLON tubing and maintained at moderately elevated temperature, e.g., 125° F., for a short period of time to allow the folded or crushed stent to temporarily maintain the shape shown in the figures. This allows the folded stent to be introduced through the catheter lumen with relative ease.

The device described herein may be used in the following manner. The inflatable stent may be attached to the tip of an infusion catheter which may be then or later filled with a medium. A guidewire is then inserted through the false lumen of the collapsed device. The assembly is then threaded into a guide catheter. The guidewire is then used to maneuver the collapsed stent assembly to the desired vascular site. The device is then pressurized to lock into position, and the catheters are then removed, thereby leaving the device in place. The stent may be filled with radiopaque contrast material to provide radiopacity to the stent. The stent alternatively may be filled with a quick-curing adhesive or gel such as HEMA having adequate curing time, mixed with a tantalum powder or the like for radiopacity. This mixture, once cured, will provide the stent with exceptional long-term patency.

The embodiments shown and described above are only exemplary. Various modifications can be made in the construction, materials, arrangement and still be within the scope of the invention found below in the claims.

I claim as my invention:

1. An inflatable stent comprising tightly, helically wound polymeric tubing forming tubing turns and having a proximal tubing end and a distal tubing end, forming a hollow column having an outer column diameter and an inner lumen extending along a stent axis from a proximal stent end to a distal stent end and having a lumen diameter, the distal tubing end being sealed and the proximal tubing end being adapted to accept an inflating fluid and having at least one flexible polymeric sizing strip laid against and adherent to the polymeric tubing from the region with the proximal stent end to the region of the distal stent end and where said at least one flexible polymeric sizing strip has a softening point below the softening point of the polymeric tubing.

2. The inflatable stent of claim 1 where the proximal tubing end adapted to accept an inflating fluid comprises a one-way valve.

3. The inflatable stent of claim 2 where the one-way valve comprises a plug of an elastomer having a slit therethrough which closes upon application with pressure within the polymeric tubing.

4. The inflatable stent of claim 1 where the tightly, helically wound polymeric tubing turns adjacently adhere to each other.

5. The inflatable stent of claim 4 where the turns are thermally welded to each other.

6. The inflatable stent of claim 1 where the one or more sizing strips are positioned generally parallel to the stent axis.

7. The inflatable stent of claim 1 where the one or more sizing strips are generally located in a spiral about the outer column diameter.

8. The inflatable stent of claim 1 where the polymer of the polymeric tubing is selected from polyethylene, polypropylene, their interpolymers and block copolymers; polyacrylonitrile, polyethylene terephthalate, and polybutylene terephthalate.

9. The inflatable stent of claim 1 where the sizing strips comprise polyethelene.

10. The inflatable stent of claim 1 which has been collapsed to form a collapsed stent having a reduced outer column diameter and having a false lumen extending from the distal stent end to the proximal stent end.

11. The inflatable stent of claim 1 also comprising at least one radiopaque marker located at at least one of the proximal stent end and the distal stent end.

* * * * *